United States Patent
Daigle

(10) Patent No.: US 8,824,743 B2
(45) Date of Patent: Sep. 2, 2014

(54) ADAPTIVE ULTRASOUND IMAGE RECONSTRUCTION BASED ON SENSING OF LOCAL MEDIA MOTION

(75) Inventor: Ronald Elvin Daigle, Redmond, WA (US)

(73) Assignee: Verasonics, Inc., Redmond, WA (US)

( * ) Notice: Subject to any disclaimer, the term of this patent is extended or adjusted under 35 U.S.C. 154(b) by 910 days.

(21) Appl. No.: 12/196,882

(22) Filed: Aug. 22, 2008

(65) Prior Publication Data

US 2009/0054770 A1 Feb. 26, 2009

Related U.S. Application Data

(60) Provisional application No. 60/957,600, filed on Aug. 23, 2007.

(51) Int. Cl.
*G06K 9/00* (2006.01)
(52) U.S. Cl.
USPC .......... 382/107; 382/100; 382/106; 382/128; 600/407; 600/424; 600/437
(58) Field of Classification Search
USPC .......... 600/407, 424, 437; 382/100, 106, 107, 382/128
See application file for complete search history.

(56) References Cited

U.S. PATENT DOCUMENTS

| | | | |
|---|---|---|---|
| 5,622,174 A * | 4/1997 | Yamazaki | 600/441 |
| 5,628,320 A | 5/1997 | Teo | |
| 5,873,830 A | 2/1999 | Hossack et al. | |
| 6,083,168 A * | 7/2000 | Hossack et al. | 600/443 |
| 6,554,770 B1 * | 4/2003 | Sumanaweera et al. | 600/443 |
| 6,860,854 B2 * | 3/2005 | Robinson | 600/447 |
| 7,052,460 B2 | 5/2006 | Liu et al. | |
| 2003/0092989 A1 | 5/2003 | Aichhorn et al. | |
| 2005/0113696 A1 | 5/2005 | Miller | |

(Continued)

FOREIGN PATENT DOCUMENTS

| | | |
|---|---|---|
| JP | 2003-220059 A | 8/2003 |
| JP | 2007-513726 A | 5/2007 |

(Continued)

OTHER PUBLICATIONS

"Adaptive Multi-element Synthetic Aperture Imaging with Motion and Phase Aberration Correction" by M. Karaman, H.S. Bilge, and M. O'Donnell, IEEE Trans Ultraso, vol. 45, No. 4, pp. 1077-1087 (Jul. 1998).*

(Continued)

*Primary Examiner* — Tse Chen
*Assistant Examiner* — Jason Ip
(74) *Attorney, Agent, or Firm* — Seed IP Law Group PLLC

(57) ABSTRACT

An image reconstruction system method for forming an image of media using data acquired from an ultrasound transducer, the method including the steps of detecting relative motion between locations in the media and the transducer; determining relative media velocity from the detecting relative motion; setting a reconstruction period for an image point based on the determined velocity; determining the amount of acquired data to use during the reconstruction period based on the reconstruction period; and using the determined amount of acquired data to reconstruct the image point for display. The system includes a data acquisition system, a processor configured to process the data, and an image display device for displaying the image.

17 Claims, 11 Drawing Sheets

(56) References Cited

U.S. PATENT DOCUMENTS

2005/0131296 A1    6/2005   Chou et al.
2005/0283077 A1*   12/2005  Rigby .................... 600/445
2007/0078342 A1    4/2007   Jago

FOREIGN PATENT DOCUMENTS

| WO | 2005023098 | A2 | 3/2005 |
| WO | 2005/059586 | A1 | 6/2005 |
| WO | 2006113445 | A1 | 10/2006 |

OTHER PUBLICATIONS

"Synthetic aperture tissue and flow ultrasound imaging" by S.I. Nikolov. PhD Dissertation. Center for Fast Ultrasound Imaging: Technical University of Denmark (2001).*

* cited by examiner

Adaptive Image Reconstruction using Media Velocity Estimation

SOFTWARE-BASED SYSTEM ARCHITECTURE

DIAGRAM OF PLUG-IN MODULE CONTAINING ACQUISITION CIRCUITRY.

New acquisition data can be combined with data in storage to improve input signal quality.

Processing results from multiple acquisitions
can be combined to improve output pixel signal.

ADAPTIVE ULTRASOUND IMAGE RECONSTRUCTION BASED ON SENSING OF LOCAL MEDIA MOTION

BACKGROUND

1. Technical Field

The present disclosure is directed to a system and process of generating an ultrasound image and, more particularly, to optimizing the reconstruction of an image for the amount of relative motion between the media and the transducer by adjusting the period of time over which acquisition data can be utilized to improve the quality of the reconstruction.

2. Description of the Related Art

Conventional ultrasound imaging systems use different acquisition methods to trade off image quality and time-motion resolution. For example, if motion in the media is low, and the ultrasound sonographer can keep a hand-held probe's motion to a minimum, acquisition and image reconstruction methods that combine multiple data sets can be used to implement features such as multiple transmit zone focusing, frequency compounding and spatial compounding—features that enhance image quality by providing improved spatial resolution and contrast detail. When the operator is moving the transducer rapidly, or there is motion in the media, which for medical applications could be due to breathing or cardiovascular pulsations, these image enhancement features are not effective, due to signal phase changes and image registration problems over the longer acquisition periods. Since these acquisition and reconstruction methods operate over the entire image space, the sonographer must choose a method suited to the amount of media motion in the diagnostic application prior to performing the scanning procedure. This limits the best ultrasound image quality to those applications with a minimal amount of media motion and for which the operator has properly chosen the correct scanning method.

In addition to the acquisition and reconstruction methods for image quality improvement mentioned above, there are also synthetic aperture techniques where multiple receive apertures are combined to produce a better image reconstruction. An example of this approach is an 'ideal' reconstruction, where a transmit is performed on each individual transducer element in the aperture while receiving on all elements. Combining the data from all of these transmit/receive acquisitions allows an image reconstruction that is in perfect focus at all points, both for transmit and receive. While the ideal reconstruction provides the best possible image resolution from a given transducer, it is almost never used in conventional ultrasound imaging systems. This is due to the long acquisition times for each image frame, during which the phase information in the returning ultrasound echoes must remain nearly stationary, so that multiple acquisitions can be combined. Any motion of the transducer or media during the acquisition phase will change the phase information and degrade the image reconstruction.

BRIEF SUMMARY

Conventional ultrasound image reconstruction often involves trade-offs between image quality factors, such as spatial and contrast resolution, and time of acquisition, which equates to frame rate. In situations where the media is in motion, acquisition times must be kept short to adequately capture motion detail and to preserve echo phase information during the image reconstruction process. An adaptive method of image reconstruction has been developed that optimizes the image reconstruction at multiple individual spatial points in the image based on a prior determination of the local media motion. At each image point, the local spatial velocity in the plane of the image is estimated and then used to set the length of the reconstruction period for that image point. For image points with low media motion, longer reconstruction periods can be used, with additional acquired spatial and frequency information brought to contribute to the reconstruction. The resulting image frame has improved overall image quality without sacrificing motion detail resolution.

In accordance with one embodiment of the present disclosure, a method of processing ultrasound images of media in which an ultrasound transducer is used to acquire imaging data is provided. The method includes acquiring ultrasound imaging data of the media from the ultrasound transducer; determining relative motion between the media and the ultrasound transducer; and processing the acquired data to generate images of the media for display in which more acquired data is utilized in image regions having lower levels of relative motion between the media and the transducer than in regions that have higher levels of relative motion for generating an image.

In accordance with another aspect of the foregoing embodiment, processing the acquired data for an image region includes processing the acquired data using at least one subset of the acquired data when the relative motion of the image region is greater than a relative motion limit and otherwise using all of the acquired data.

In accordance with another aspect of the foregoing embodiment, processing the data for an image region includes processing the data using at least one subset of the acquired data when the relative motion of the image region is greater than a relative motion limit and using at least one additional subset of the acquired data when the relative motion falls below one or more descending motion limits.

In accordance with another aspect of the foregoing embodiment, acquiring ultrasound imaging data includes generating an acoustic signal; receiving at least one echo of the acoustic signal at a plurality of receiving elements and obtaining an echo signal therefrom; storing each echo signal from each of the plurality of receiving elements; mapping a given pixel into a region of the stored echo signals; organizing the mapped region of the stored echo signals into an array for the given pixel; and processing the acquired data includes processing the array to generate a response for the given pixel; and using the response to obtain acoustic information for the given pixel.

In accordance with another embodiment of the present disclosure, an ultrasound processing method is provided that includes generating an acoustic signal with a transducer; receiving at least one echo from the acoustic signal and acquiring echo signal data therefrom, and detecting relative motion between the media and the transducer at an image construction point; storing the acquired echo signal data from each of a plurality of receiving elements; mapping a given pixel into a region of the stored acquired echo signal data; organizing the mapped region of the stored acquired echo signal data into an array for the given pixel; and determining whether the relative motion exceeds a limit, and processing the array for each pixel using a subset of acquisition data when the relative motion between the media and the transducer exceeds the limit and otherwise using all acquisition data when the relative motion between the media and the transducer does not exceed the limit.

An image reconstruction method for forming an image of media using data acquired from an ultrasound transducer is provided, the method including detecting relative motion between locations in the media and the transducer; determining relative media velocity from the detected relative motion; setting a reconstruction period for an image point based on the determined velocity; determining the amount of acquired data to use during the reconstruction period based on the setting of the reconstruction period; and using the determined amount of acquired data to reconstruct the image point.

In accordance with another aspect of the present disclosure, the output of the processing methods disclosed herein is generally used to generate an image for display on a display device, such as a monitor or projector, or for printing on a printer, or transmission to another device for subsequent processing, display, or operation of the other device, or any combination of the foregoing.

In accordance with another embodiment of the present disclosure, a system is provided for reconstruction of an image of media, the system includes a data acquisition system adapted to acquire data from the media to detect relative motion between locations in the media and the transducer; a processor adapted to determine relative media velocity from the detected relative motion, to set a reconstruction period for an image point based on the determined velocity, and determine the amount of acquired data to use during the reconstruction period based on the setting of the reconstruction period; and a device coupled to the processor for displaying an image of the media.

In accordance with another aspect of the system, the processor is configured to use the pixel-oriented processing to generate the image data.

DETAILED DESCRIPTION

Figure 1:
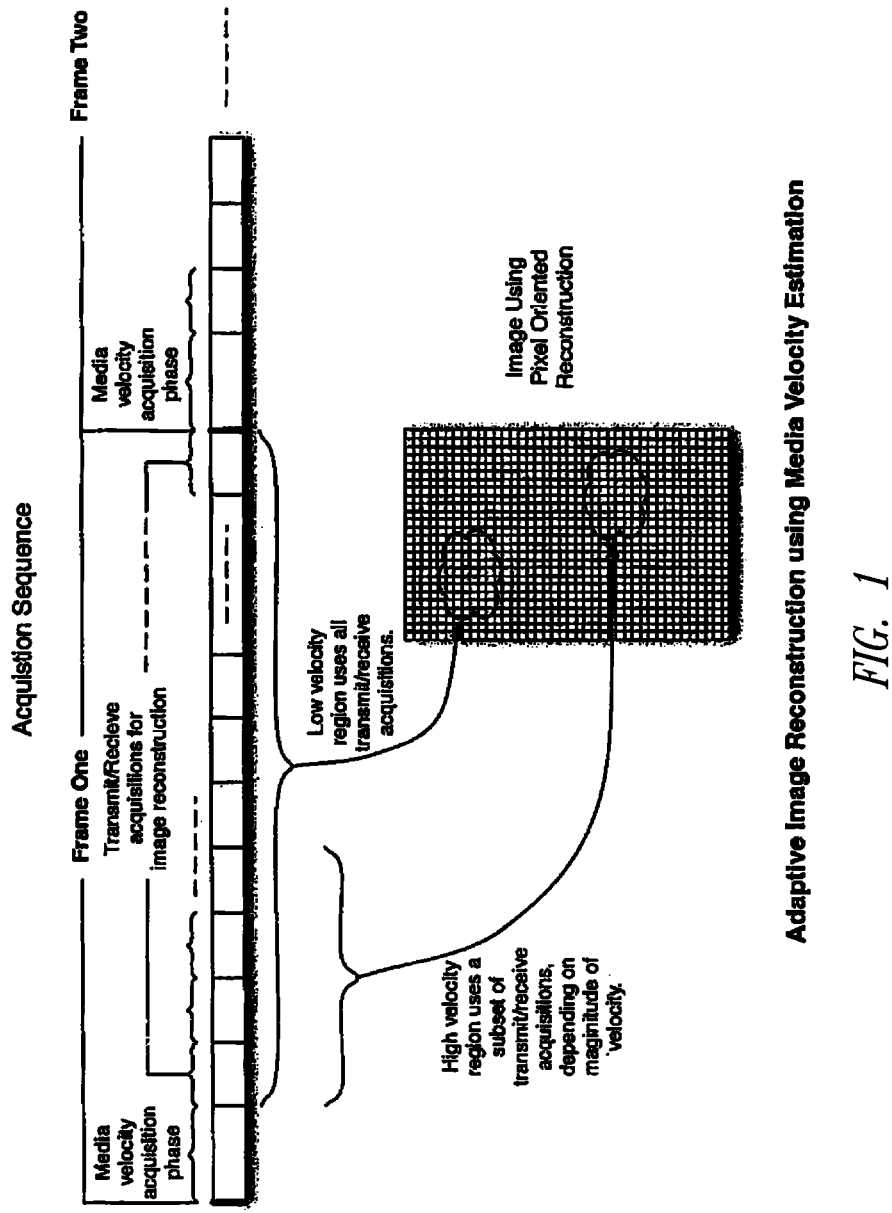
FIG. 1 is an illustration of adaptive image reconstruction using media velocity estimation.

In the following description, one skilled in the relevant art will recognize that embodiments may be practiced without one or more of the specific details described in the Specification, or with other methods, components, materials, etc. In other instances, well-known structures have not been shown or described in detail to avoid unnecessarily obscuring descriptions of the embodiments.

Unless the context requires otherwise, throughout the Specification and claims which follow, the word "comprise" and variations thereof, such as, "comprises" and "comprising," and "including" and variations thereof, such as "included," are to be construed in an open, inclusive sense, that is as "including, but not limited to."

References throughout this specification to "one embodiment" or "an embodiment" means that a particular feature, structure or characteristic described in connection with the embodiment is included in at least one embodiment. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this Specification and the appended claims, the singular forms "a," "an," and "the" include plural referents unless the content clearly indicates otherwise. It should also be noted that the term "or" is generally employed in its sense including "and/or" unless the content clearly dictates otherwise.

For purposes of clarity and ease of comprehension, terms such as pixel-oriented processing may be used to indicate a method of processing ultrasound data but are not intended to limit the scope of the invention. For ease of reference and for descriptive purposes, the processing environment of applicant's prior U.S. patent application Ser. No. 11/911,633, entitled ULTRASOUND IMAGING SYSTEM WITH PIXEL ORIENTED PROCESSING, which is incorporated herein in its entirety, may be used, but should not be interpreted as limiting.

Adaptive Reconstruction—

Using software-based processing methods, particularly pixel-oriented image reconstruction methods, it is possible to combine different reconstruction schemes on individual pixels within the same image frame. With an appropriate acquisition sequence, this allows optimizing the reconstruction at each image point for the amount of motion in the media. The lower the media motion is at the pixel point, the longer the period over which acquisition data can be utilized to improved the quality of the reconstruction of the pixel point.

In general, the adaptive reconstruction method is implemented as follows: 1) A multiple transmit/receive acquisition sequence is chosen for the imaging application that can be executed in a time period corresponding with the desired real-time frame rate. For typical applications, frame rates in the vicinity of 20-30 frames per second are usually adequate, which translate to acquisition sequences as long as 50 to 33 msec. 2) A pre-amble to each image acquisition sequence is added that allows detection of the media motion at each reconstruction point in the image. 3) The image is reconstructed at each image point, using the motion estimate to specify how much of the full acquisition sequence can be recruited in the reconstruction process.

Synthetic Aperture Adaptive Reconstructions—

Figure 2:
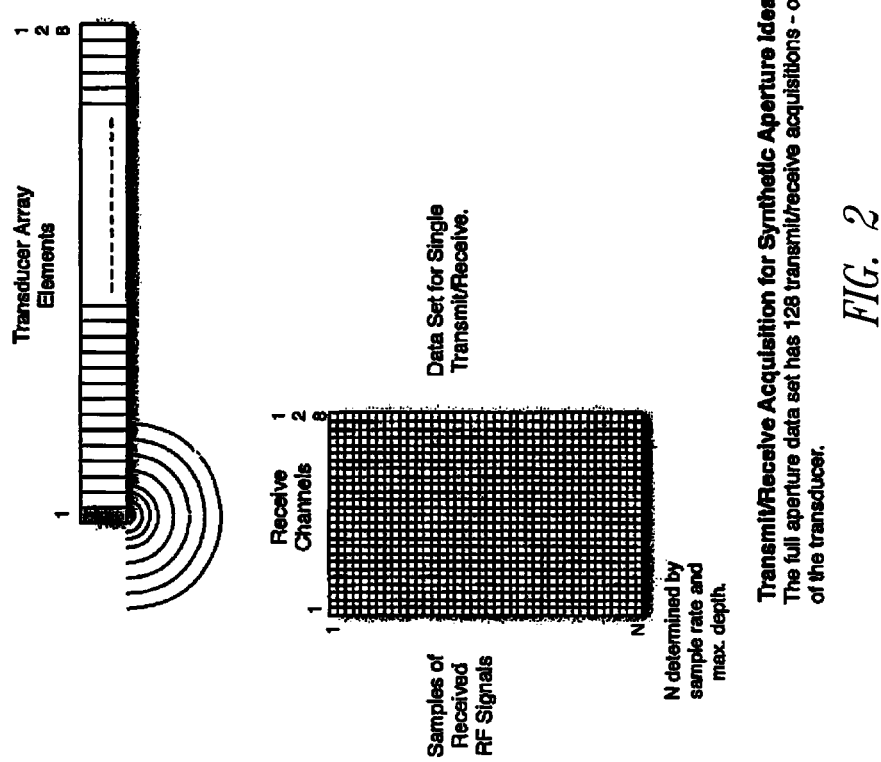
FIG. 2 is an illustration of a transmit/receive acquisition for synthetic aperture ideal reconstruction.

In one embodiment of the adaptive reconstruction technique, the acquisition phase consists of a series of synthetic aperture acquisitions for each image frame. As an example, consider the 'ideal' reconstruction method described above. For each acquisition frame, a transmit-receive cycle is performed for each element in the transducer, as shown in FIG. 2. A 128 element transducer would then require 128 transmit-receive cycles, with the single element transmitter stepped across each element in the array. On receive, all elements in the array are used, and the data from all 128 elements are stored in a memory system on each cycle for later processing. The acquisition of the entire frame of data requires 128 transmit-receive periods, whose length is determined by the imaging depth. Since ultrasound travels at about 1540 m/s in the human body, a typical imaging depth of 10 cm requires a receive period of about 130 usec, which is the round trip travel time of an ultrasound pulse from the transducer to the maximum depth and back. In this typical case, the 128 transmit-receive cycles for an 'ideal' reconstruction frame would take about 17 msec, providing more than adequate frame rate for most applications.

If there is no motion in the media, the individual element receive data acquired over the full 17 msec period in the example above can be combined to yield an ideal reconstruction, providing the best possible image for the transducer aperture. However, in typical imaging situations, there may be media motion or transducer motion that prevent combining all of the data. If the phase of the ultrasound signal at a reconstruction point in the media changes by more than about ⅛ of a wavelength of the ultrasound pulse over the 17 msec period, the reconstruction will be compromised, and resolution will be degraded. For a typical ultrasound pulse frequency of 3 MHz (wavelength 0.5 mm), this means that movement in the media must be less than (⅛*0.5)=0.0625 mm in 17 msec, or 3.7 mm/sec. This is a fairly low velocity that can easily be exceeded by probe movement or internal motion within the body as might be caused by breathing or cardiovascular pulsations. Consequently, the full 17 milliseconds of acquisition data can only be used under the best circumstances of probe or media motion.

If the media velocity is known with respect to the transducer probe at each pixel point in the image region, this information can be used to determine the amount of acquisition data that can be combined for the image reconstruction at that point. To obtain the media velocity information, a Doppler technique can be used in which only a few pulse transmissions are used to estimate the tissue velocity at all points in the image. One such technique utilizes transmit pulses with a flat wavefront over the entire transducer aperture, which insonifies the entire image field at once. Comparing the phase change of the reconstructed ultrasound signal at each image point from one pulse to the next provides an estimate of the media velocity in the direction of the probe, since the velocity at a point can be equated to the rate of change of phase. To obtain the phase shift, one of two algorithms is generally used—the Kasai algorithm or cross-correlation. Inasmuch as these and other methods are known to those skilled in the art, they will not be described in detail herein.

If the estimate of the media motion at a reconstruction point exceeds the 3.7 mm/sec limit calculated above, we can use a subset of the acquisition data to reconstruct an image point. If we assume an upper limit of motion in the media (towards or away from the probe) of 60 mm/sec (this limit might be raised or lowered, depending on the application), the ⅛ wavelength criteria used above limits our acquisition period to around 1.04 msec. For the 130 usec period in our example, the number of transmit/receive periods would then be limited to approximately eight. In the case of the ideal reconstruction, the transmit/receive events can be ordered so that the first eight events use transmitting elements that are spaced equally across the aperture of the array. Subsequent events gradually fill in the spaces between the first eight transmitting elements until all elements have been utilized (See FIG. 3). This ordering then provides 16 groups of 8 acquisitions each that cover the full aperture. The velocity estimate at the reconstruction point is then used to determine how many of these sets can be combined—from one set at the maximum velocity of 60 mm/sec, to all 16 sets below 3.7 mm/sec.

Figure 3:
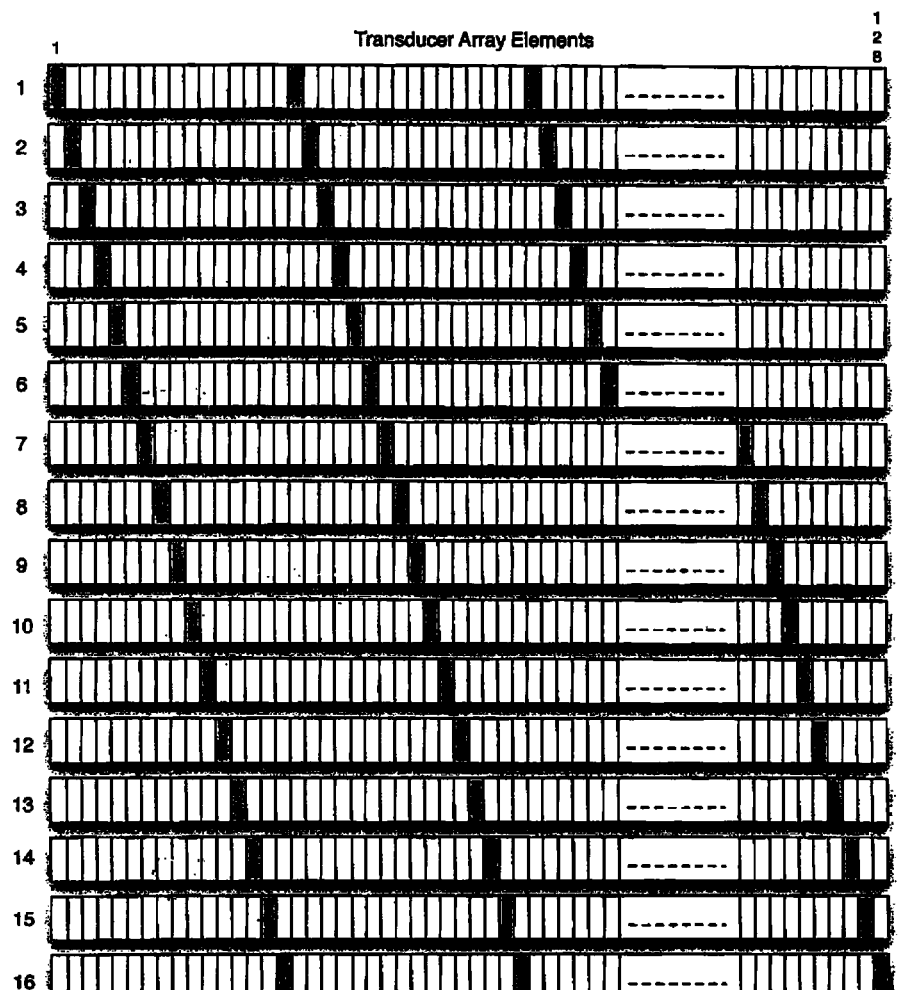
FIG. 3 is an illustration of transmit receive acquisition groups for ideal reconstruction.

It is recognized that there are other ways of sequencing acquisitions and forming groups of acquisitions, than the method shown in FIG. 3, so that more optimal image reconstructions are obtained when only a few groups are utilized. The scheme in FIG. 3 attempts to maximize the size of the aperture in each of the groups of eight acquisitions, which improves lateral resolution when only a few groups are utilized in the reconstruction; however, the sparse sampling of the aperture in each group leads to increased spurious reconstruction artifacts and decreased contrast resolution. Other acquisition sequences could be used to try and improve on this tradeoff of spatial and contrast resolution; for example, instead of an equal spacing of the transmitting element in the eight acquisitions of a group, a more random spacing could be utilized in each group (without repeating a transmit on a given element), which would tend to diffuse the reconstruction artifacts.

In another possible sequence of acquisitions, the transmitting element can simply be stepped across the aperture in sequential order from left to right. For each image reconstruction point, a number of acquisitions are selected for reconstruction by selecting acquisitions whose transmitters are nearest to the normal of the transducer face that passes through the reconstruction point. The number of transmit/receive acquisitions utilized in a reconstruction is determined by the media motion and the aperture expands outward from the normal. If the media motion at the reconstruction point is lower than the motion limit (3.7 mm/sec in the example above), the full aperture can be used for reconstruction (all 128 transmit/receive events). This scheme maximizes contrast resolution when only a few acquisitions are utilized, at the expense of lateral resolution.

With the method described above, the reconstruction of an individual image point or pixel is adapted to the amount of movement of the media at that point. If the transducer probe is held stationary by the operator, the amount of information that goes into the reconstruction of each image point is determined solely by media movement—in areas where there is little or no movement, the quality of the reconstruction can be substantially improved over areas with larger amounts of movement. Similarly, if the operator is moving the probe rapidly to assess a region of interest, the reconstruction period is reduced, allowing for rapid tracking of the probe motion. When the operator homes in on a specific region and holds the probe stationary, the reconstruction period extends, providing a higher quality image.

There are many possible combinations of synthetic aperture acquisitions that can make use of the adaptive reconstruction method described above. Another example is based on the flat wavefront transmit scheme mentioned above as a possible mechanism for detecting the velocity in the media. The flat wavefront transmit method can be used to produce images at high frame rates, since only a single transmit pulse can be used to generate the entire image. However, a single pulse image suffers from reduced lateral resolution, due to the lack of focusing on transmit. For improved image resolution, it is possible to combine the receive data from multiple flat wavefront transmit pulses that have been altered in various ways to provide additional echo phase and amplitude information. As an example, consider the case of a linear transducer array, where a flat wavefront transmit waveform can be steered over a number of angles for an acquisition data set. When the spatially reconstructed data are combined in phase and amplitude, the resulting image has significantly improved spatial and contrast resolution.

In a specific implementation of the linear array flat wavefront imaging method, each of 21 transmit and receive acquisitions could utilize a different flat wavefront steering angle from −20 degrees to +20 degrees at one degree increments. A low motion reconstruction point could then utilize all acquisitions, combining the receive data in both amplitude and phase, to provide a best case reconstruction. For a reconstruction point where media movement has been detected, a subset of the acquisitions could be used, spread over the range of steering angles. Again, the number of acquisitions used would be chosen based on the criterion that phase information is not degraded by the motion. This adaptive reconstruction would then provide significantly improved image quality for low motion areas of the image field, without compromising time motion resolution in areas of the field with high motion.

Other Adaptive Reconstruction Methods—

In addition to the many combinations of synthetic aperture acquisitions, there are also adaptive reconstruction methods that operate using other ultrasound imaging techniques, such as frequency and spatial compounding. For imaging using traditional frequency compounding, multiple acquisitions are made using different ultrasound center frequencies for both transmit and receive processing. When the results are combined, the speckle artifacts in the image are reduced. With spatial compounding, the transmit beams are steered over multiple angles to insonify targets from multiple directions. The resulting images are generally combined using multiplicative averaging of the amplitude information. Since these methods typically combine full image frames, the improvement in image quality comes at the expense of reduced frame rate.

Figure 4:
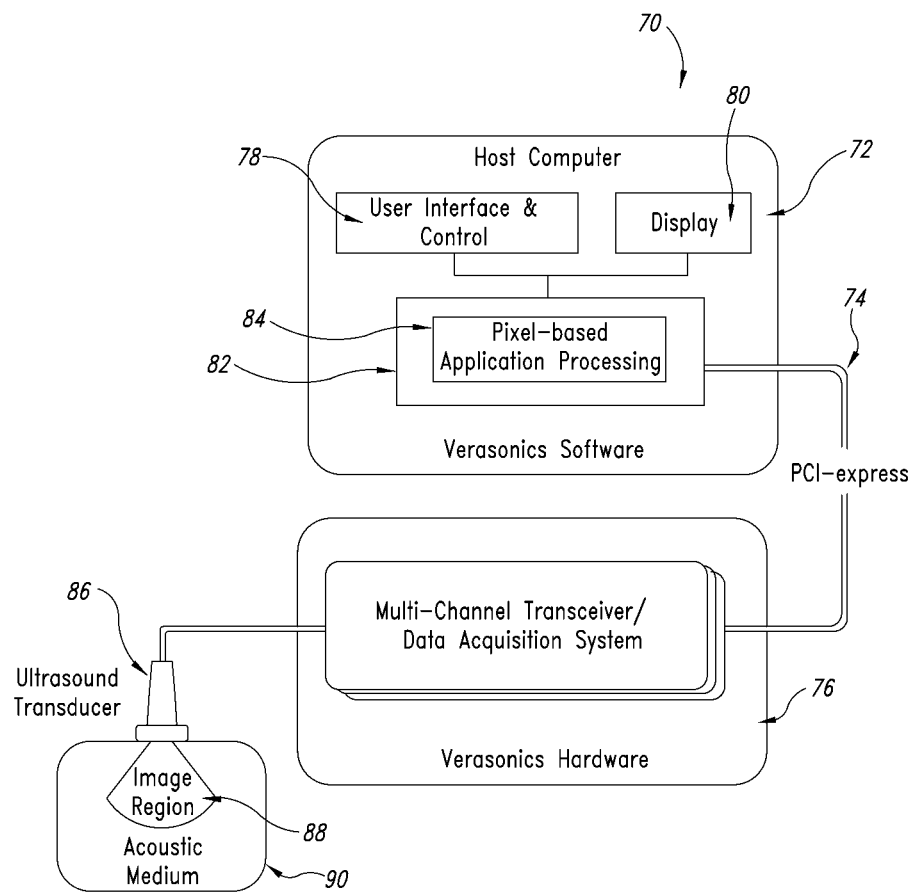
FIG. 4 illustrates a high-level representation of the system architecture for the processes of the present disclosure.

FIG. 4 is a system level block diagram that represents a high-level system architecture 70 for implementing the processes of the present disclosure. It is to be understood that this is merely one representative embodiment, and the illustrated architecture 70 is not a requirement for all embodiments of the present disclosure.

The architecture 70 includes a host computer 72 coupled via a PCI-express 74 to a multi-channel transceiver and data acquisition system 76. The host computer 72 has a user interface and control 78, and a display 80, both coupled to a processor 82 that utilizes the pixel-based application processing software 84. The multi-channel transceiver and data acquisition system 76 hardware are coupled to an ultrasound transducer 86 that is used to image a region 88 in an acoustic medium 90 for display on the display 80, such as a monitor, projector, or for transmission to another device for display or operation of the device or both. Because these components are readily commercially available, they will not be described in detail herein.

Using pixel oriented processing allows for adaptive reconstructions that incorporate various degrees of frequency and/or spatial compounding. In this method, multiple frames of image data are acquired using acquisition methods that provide a relatively high frame rate. Interleaved with the normal frame acquisitions are periodic acquisition sequences for determining media velocity at the image points. The preferred method of media velocity measurement is the flat wavefront transmit method described earlier, which can estimate media velocity at all image points with only a few transmit/receive cycles. The media velocity estimate at an image point is then used to determine how many frames of image data can be combined. The image data at the corresponding image point in each of the acquired frames is then combined, typically using arithmetic or multiplicative averaging to produce the displayed image value.

Figure 5:
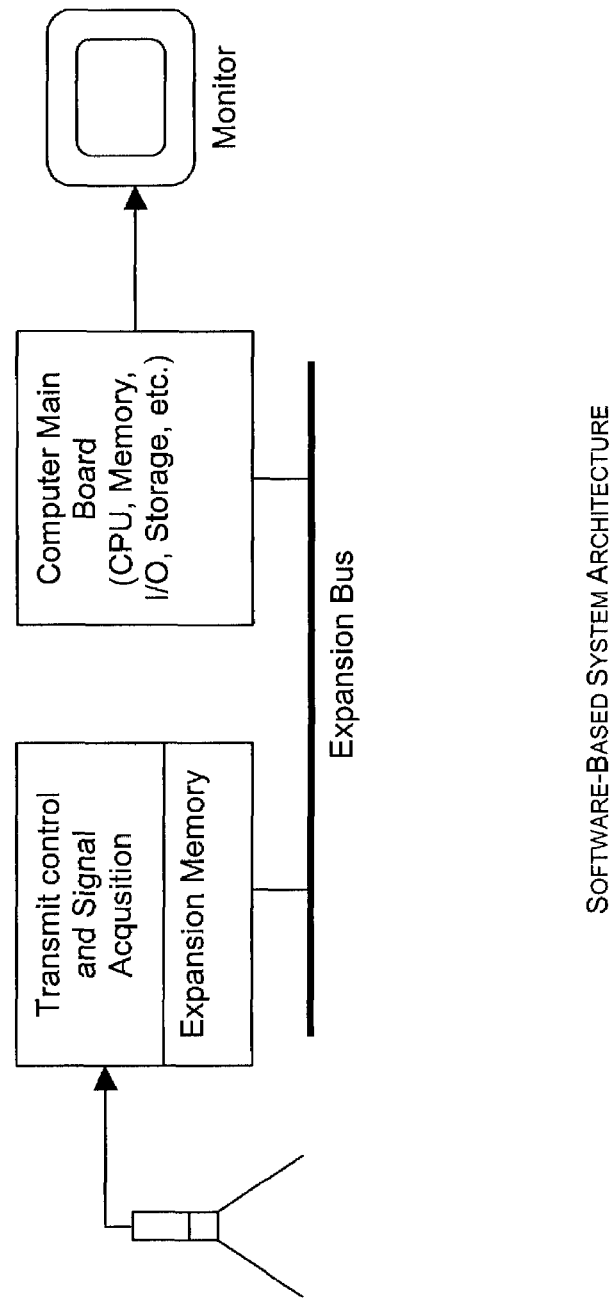
FIG. 5 is a schematic representation of the a software-based architecture of one embodiment of the present invention.

A software-based method and system architecture in accordance with one embodiment of the present disclosure implements all real-time processing functions in software. The proposed architecture is shown schematically in FIG. 5.

The only custom hardware component in the software-based system is a plug-in module to the expansion bus of the computer that contains the pulse generation and signal acquisition circuitry, and a large block of expansion memory that is used to store signal data. The signal acquisition process consists of amplifying and digitizing the signals returned from each of the transducer elements following a transmit pulse. Typically, the only filtering of the signals prior to digitization, other than the natural band-pass filtering provided by the transducer itself, is low pass, anti-aliasing filtering for A/D conversion. The signals are sampled at a constant rate consistent with the frequencies involved, and the digitized data are stored in memory with minimal processing. The straightforward design of the signal acquisition allows the circuitry to be implemented with off-the-shelf components in a relatively small amount of board area.

Figure 6:
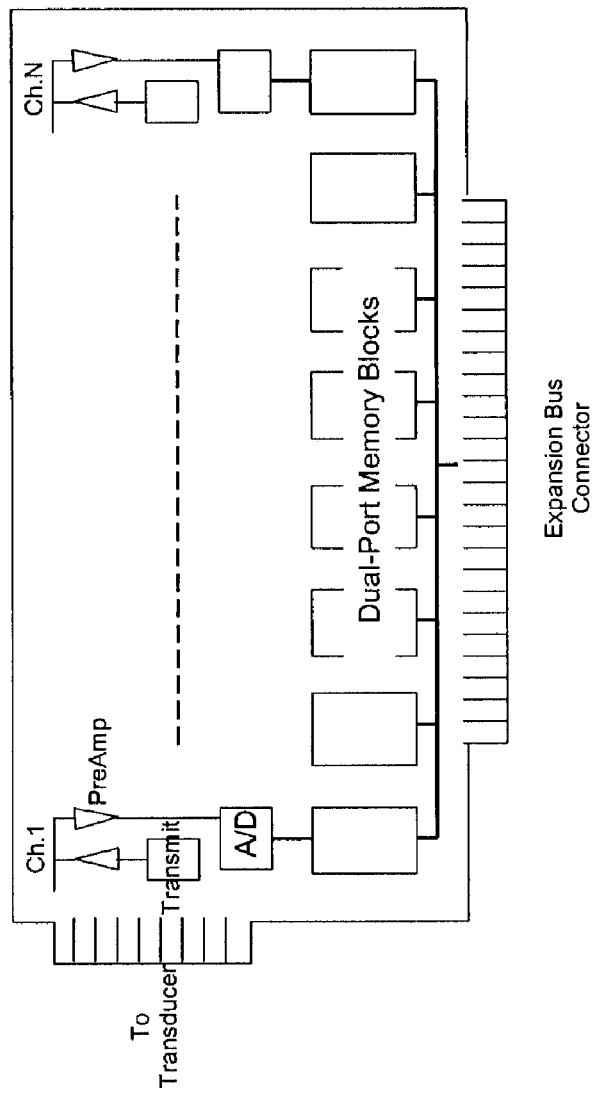
FIG. 6 is a diagram of a plug-in module formed in accordance with one embodiment of the present invention.

A more detailed look at the plug-in module is shown in FIG. 6. Multiple acquisition channels are shown, each composed of a transmitter, receiver pre-amplifier, A/D converter, and memory block. During reception, the transducer signals are digitized and written directly to the individual memory blocks. The memory blocks are dual-ported, meaning they can be read from the computer side at the same time acquisition data is being written from the A/D converter side. The memory blocks appear as normal expansion memory to the system CPU(s). It should be noted that the size of the plug-in module is not limited to the normal size of a standard computer expansion card, since the system is preferably housed in a custom enclosure. Also, multiple plug-in modules can be used to accommodate a large number of transducer elements, with each module processing a subset of the transducer aperture.

The components for the plug-in module, including amplifiers, A/D converters and associated interface circuitry, and the needed components for transmit pulse generation and signal acquisition are readily commercially available components and will not be described in detail herein. The memory block needed for RF data storage of echo signals obtained from received echoes is essentially the same circuitry as found in commercially available plug-in expansion memory cards, with the addition of a second direct memory access port for writing the digitized signal data. (The received echo signal data is generally referred to as RF data, since it consists of high frequency electrical oscillations generated by the transducer.) The memory is mapped into the central processor's address space and can be accessed in a manner similar to other CPU memory located on the computer motherboard. The size of the memory is such that it can accommodate the individual channel receive data for up to 256 or more separate transmit/receive cycles. Since the maximum practical depth of penetration for round trip travel of an ultrasound pulse in the body is about 500 wavelengths, a typical sampling rate of four times the center frequency will require storage of as many as 4000 samples from an individual transducer element. For a sampling accuracy of 16 bits and 128 transducer channels, a maximum depth receive data acquisition will require approximately one megabyte of storage for each transmit/receive event. To store 256 events will therefore require 256 MB of storage, and all totaled, a 128 channel system could be built on a few plug-in cards.

Another aspect of the software-based ultrasound system is the computer motherboard and its associated components. The motherboard for the proposed design should preferably support a multi-processor CPU configuration, for obtaining the needed processing power. A complete multi-processor computer system, complete with power supply, memory, hard disk storage, DVD/CD-RW drive, and monitor is well-known to those skilled in the art, can be readily commercially purchased, and will not be described in greater detail.

Pixel-Oriented Processing

While other processing methods can be used to implement the adaptive reconstruction methods described above, the preferred processing method uses pixel-oriented processing. An ultrasound image has a fundamental resolution that depends on the physical parameters of the acquisition system, such as the frequency and array dimensions, and can be represented as a rectangular array of pixel values that encode echo amplitude or some other tissue (acoustic) property. The density of this rectangular pixel array must provide adequate spatial sampling of the image resolution. (It is recognized that display images need not consist only of rectangular arrays of pixels, but could consist of any arbitrary set of pixels, representing different geometric shapes.)

The next step is to start with one of the pixels in this image array and consider which sample points in the RF data set contribute to the calculation of this pixel's intensity, and determine the most efficient way of accessing and processing them. This approach is a completely different approach than the one utilized by existing ultrasound systems, which use a flow-through architecture, since only information that contributes to pixels on the display needs to be processed. In this the approach, a small region on the display image region will take less overall processing time than a large image region, since because the small region contains fewer pixels. In contrast, the flow-through processing methods must be designed to handle the maximum data stream bandwidths, independent of the image region size.

After processing the pixel array required to adequately represent the ultrasound image, the array can be rendered to the computer display at an appropriate size for viewing. The graphics processor of the computer, requiring no additional CPU processing, can typically carry out this operation, which consists of simple scaling and interpolation.

Figure 7:
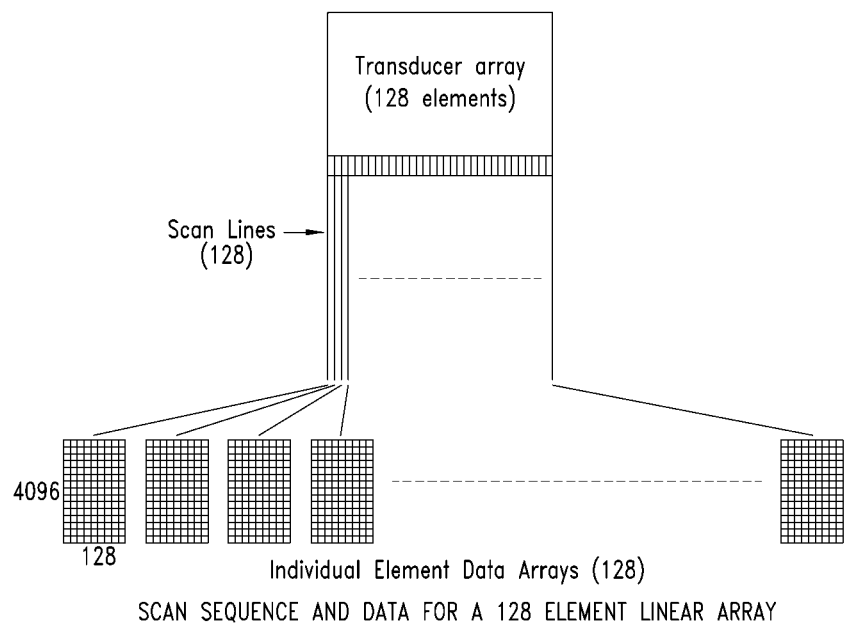
FIG. 7 is a schematic representation of the acquisition data for a 128 element linear array formed in accordance with the present invention.
Figure 8:
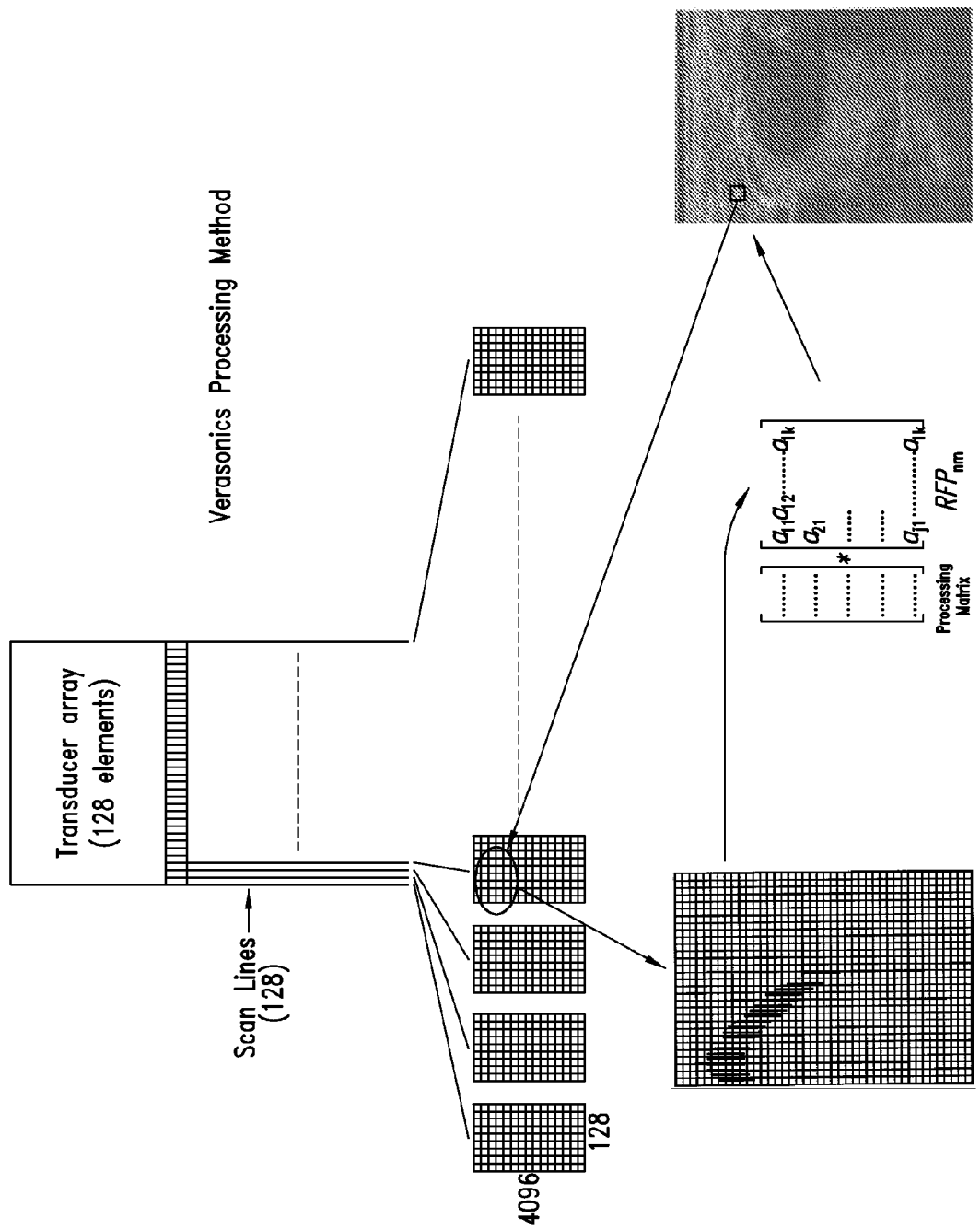
FIG. 8 is an illustration of a reverse pixel mapping process of the present invention.

The processing strategy for a single pixel of the ultrasound image is next considered. In this discussion, it is assumed that the objective is to obtain the echo intensity at the corresponding spatial location of the pixel with respect to the transducer array. Other acoustic parameters may be similarly obtained. The first step is to find the region of acquisition RF data containing samples that contribute to the echo intensity calculation. To accomplish this for the scanning method of FIG. 7, the acquisition scan line that comes closest to intersecting the pixel location must first be found, and then the corresponding individual element data array is used. FIG. 8 shows this mapping process for an example pixel in an ultrasound image.

In FIG. 8, the indicated pixel maps to the closest acquisition line of the scan, which in this case is scan line 4, whose RF data resides in the fourth individual element RF data array (which represents data collected from the fourth transmit/receive event). More than one RF data array could be chosen as contributing to the pixel signal, but for this example we will consider only a single data array.

The next step is to map out the region in the individual element array containing samples that contribute to the pixel's intensity calculation. This mapping process is fairly complex and depends on several factors. The transducer elements each have a region of sensitivity that determines how they will respond to a signal returning from a particular point in the image field. For a given image point, only elements that have sensitivities above a predetermined threshold need be considered, since if the sensitivity is too low, an element will not contribute useful information to the pixel's quantity. This sensitivity threshold then determines the number of element data columns to include in the mapped region. As shown in FIG. 8, elements on the far right hand side of the transducer are not included in the mapped data region.

The starting depth of the mapped data region is determined by the arrival time of the returning echo at each individual transducer element. As shown in FIG. 8, the image point signal for elements further away from the image point is captured later in time, and so the starting point of the data set is deeper in memory. Finally, the depth range needed for the mapped data region is dependent on the duration of the transmit pulse generated. Longer transmit pulses will excite the image point for a longer period of time, generating echo signals that extend over a larger depth span of the RF memory.

Fortunately, many of the factors that go into determining the region of mapped data can be pre-computed for a given pixel grid, since this grid does not change over the multiple frames of a real-time image sequence. Using pre-computed factors, the mapped data region for a given pixel can be rapidly and efficiently determined, saving considerable computations during real-time imaging.

After selecting out the reverse pixel mapped RF data, it can be organized into a matrix, $RFP_{nm}$, as shown below.

$$RFP_{nm} = \begin{bmatrix} a_{11} a_{12} & \cdots & a_{1k} \\ a_{21} & & \\ \cdots & & \\ \cdots & & \\ a_{j1} & \cdots & a_{jk} \end{bmatrix}$$

The notation '$P_{nm}$' refers to the image pixel in row n, column m. The matrix columns are the vertical bars of FIG. 8 where it is assumed that the number of samples, j, in each vertical bar are the same. The number of samples, j, is dependent on the range of RF data in time needed for capturing the signal generated by the transmit pulse. The index, k, is the number of channels in the RF data array that have adequate signal strength from to the image point to participate in the intensity calculation.

The process of computing the signal intensity value of pixel $P_{nm}$ now consists of a series of matrix operations that eventually lead to a single value. When the computations are organized in this fashion, it quickly becomes apparent that some of the matrix operations may be algebraically combined, leading to fewer computational operations. Without going into specific details, the operations of sample interpolation to find the correct delay values for individual elements, bandpass filtering, Hilbert transform filtering for quadrature detection, and final summation can be performed in a single matrix multiply, then taking the trace of the resulting matrix (The trace of a matrix is the sum of the elements along the main diagonal. Since only the main diagonal of the result of the matrix multiply is needed, the multiply operation can be considerably simplified).

Since many of the matrices needed for these operations are independent of the pixel location, they can be pre-computed prior to real-time operation. The processing matrix can then be formed by combining pre-computed elements with elements that change dynamically with the pixel location (such as interpolation parameters). With a fixed number of interpolation steps, it is even possible to select the rows of the processing matrix from a collection of pre-computed vectors. The use of pre-computed data for forming the processing matrix, while not essential to the method, can substantially reduced processing time for real-time operation.

The signal value derived from the pixel oriented processing is typically a complex signal value, which can be represented by quadrature samples I, and Q. To obtain the echo intensity at our image point, the magnitude of the signal is computed, using a simple square root of the sum of the squares of the quadrature samples. If phase information is needed (as for additional processing for Doppler sensing), the complex signal representation can be retained.

With this computational approach, the number of processing steps required to compute a pixel's reconstructed signal value are reduced substantially over the flow-through architecture. Estimates derived from sample calculations indicate that for typical image sizes, operation reductions as great 10-to-1, a full order of magnitude, are possible. Moreover, the matrix operations needed can be carried out using the vector processing capabilities of modern processors, where multiple data can be operated on using single instructions (These instructions are called 'SIMD' instructions, which stands for 'single instruction, multiple data.' For example, the Altivec processing unit of the PowerPC can perform a multiply and accumulate on two vectors, containing eight 16-bit samples each, in a single clock cycle). These factors make it feasible to perform real-time processing of ultrasound image data using one or more general-purpose processors.

It is important to note that for the typical imaging scan, the pixel oriented processing method generates no intermediate data sets—the processing method goes directly from unprocessed acquisition acquired RF data to pixel intensity, through a simple series of matrix operations on the partitioned mapped acquisition data. Each pixel of the output image maps to its own unique region of the acquisition data, and has its own processing matrix, allowing a direct conversion from raw acquisition data to the desired acoustic signal estimate. This is not the case with the traditional flow-through architecture, which typically processes the individual channel RF data to beamformed RF samples along transmit/receive ray lines, and then generates a detected amplitude data set which that is then scan converted for display. In the pixel oriented processing method, even the process of scan-conversion, which for a sector format scan involves polar-to-rectangular coordinate conversion, is included in the single processing operation.

For irregular shapes of image data, it is more appropriate to consider the collection of pixels to be rendered as a pixel set. The actual display presented to the user can then consist of multiple pixel sets processed and rendered as a display frame. This concept is useful for implementing complex scan formats, as well as the various standard modes of ultrasound scanning, such as 2D imaging combined with Doppler imaging, 2D imaging combined with time-motion imaging (M-mode), or 2D imaging combined with spectral Doppler display. In the case of time-motion imaging and spectral Doppler, the pixel set might consist of a single pixel column, which is moved sequentially across the display.

The flexibility of the new software-based ultrasound architecture provides other advantages over the standard flow-through architecture. Previously, we have described how the new pixel-oriented processing methods can be used to implement standard ultrasound imaging acquisition modes. Since individual channel RF data are captured in memory, alternate modes of ultrasound imaging can also be supported. A significant example is often referred to as the 'uniform illumination imaging method,' or 'flash transmit method.' In this approach, the entire image field is interrogated at once with a single, unfocused transmit pulse, followed by acquisition of the returned echo signals from each individual element in the transducer array into a memory buffer. With suitable processing of the individual element data, an entire image plane can be reconstructed, without the need for further transmit pulses. The flash transmit technique can therefore acquire a full image in the same time it takes to acquire a single scan-line using the conventional method, providing theoretical frame rates as much as 128 times higher than a typical scan.

Figure 9A:
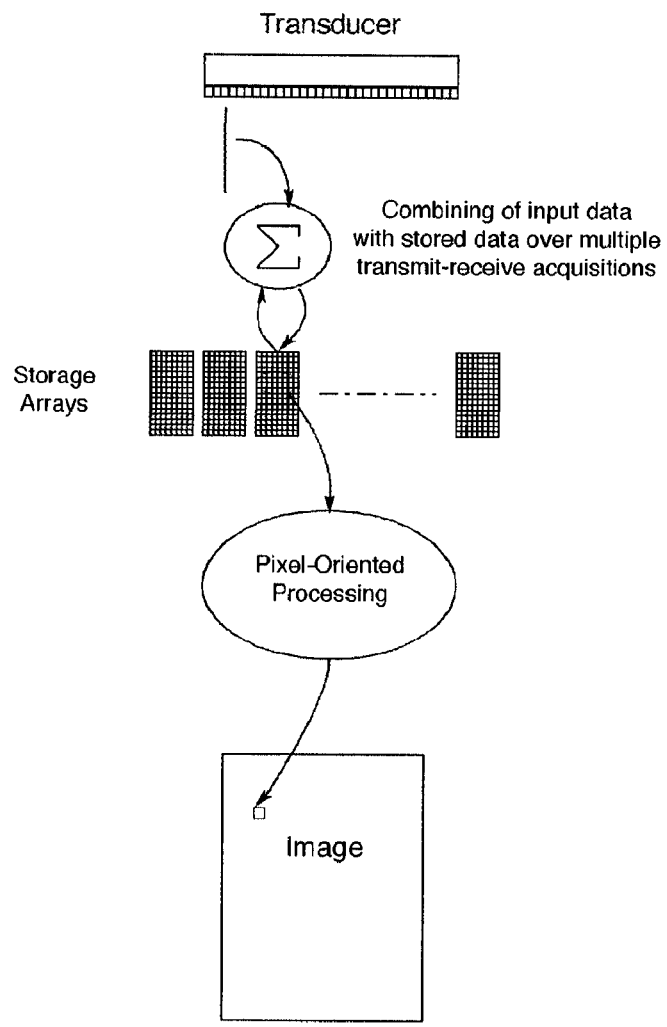
FIGS. 9A-9C illustrate alternative processing methods.
Figure 9B:
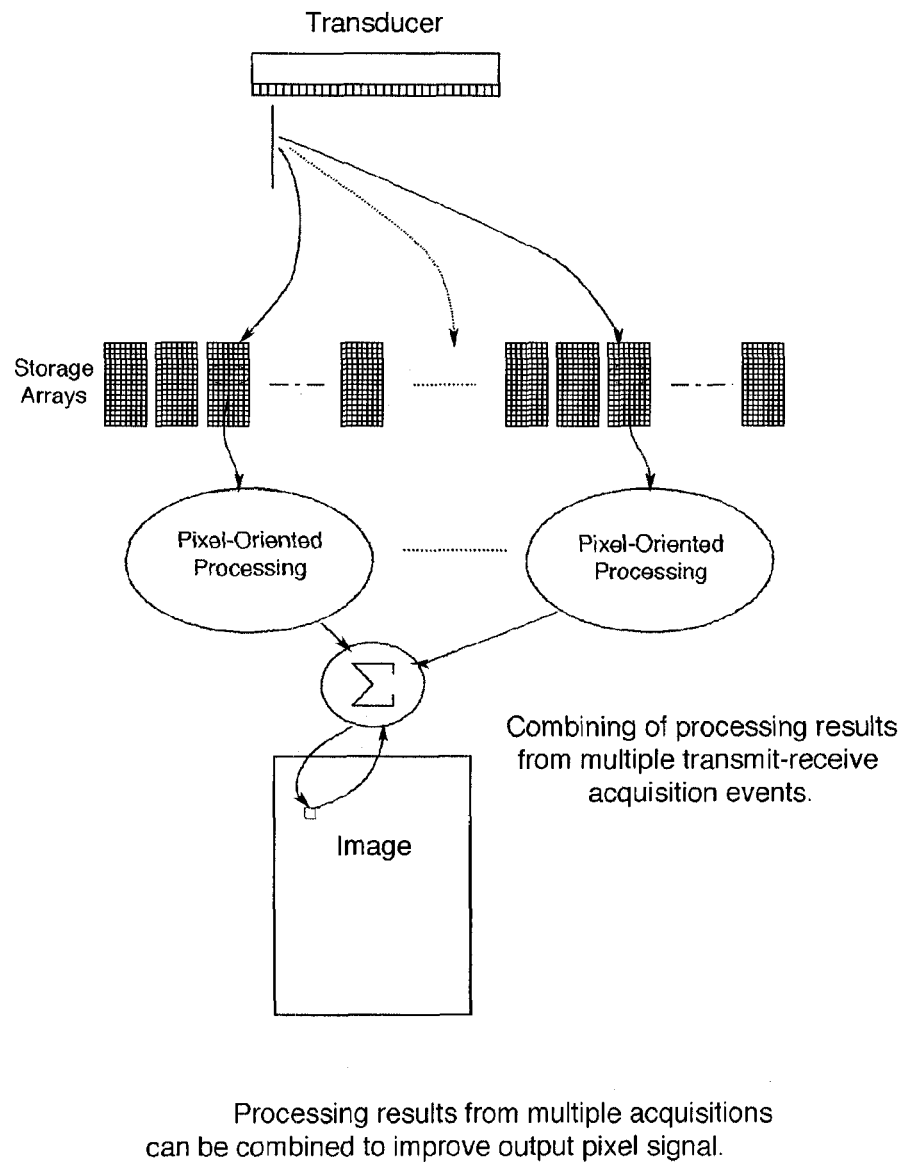
Figure 9C:
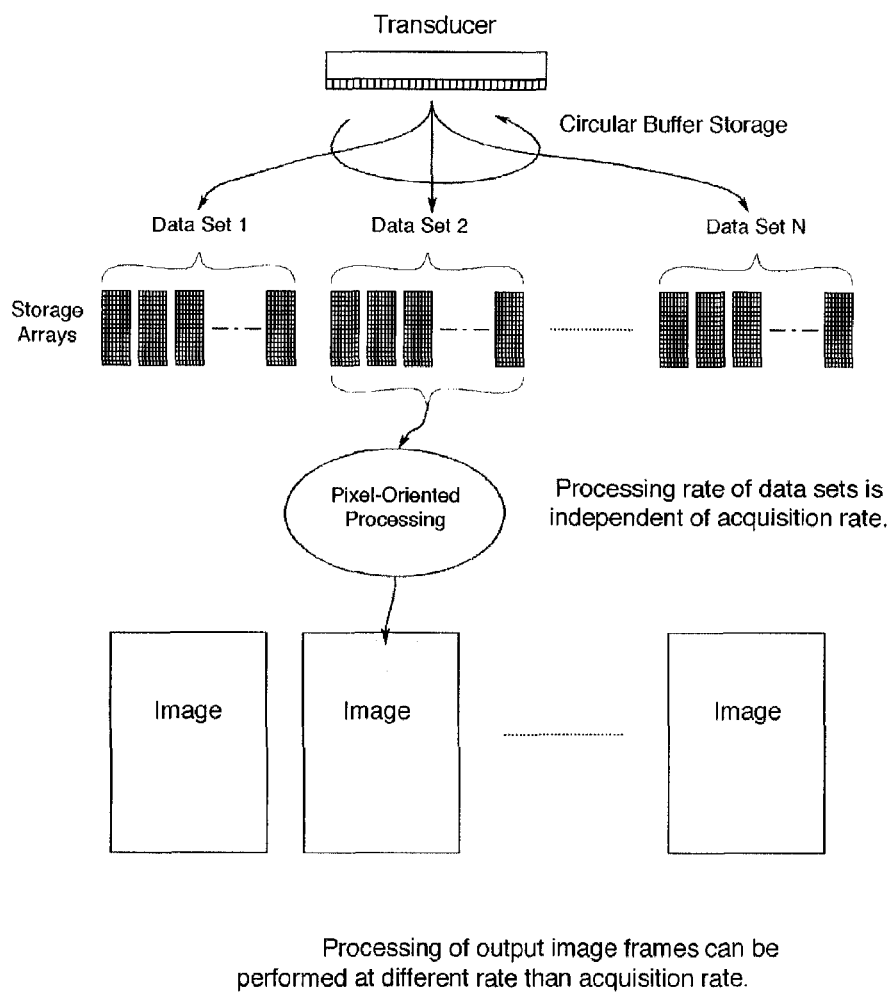

FIGS. 9A-9C summarize the variations in the pixel oriented processing method as described above. FIG. 9A shows the combining of received echo signals with signals that have been previously stored in the storage arrays. This allows such functions such as signal averaging of multiple transmit-receive acquisitions to enhance and improve signal-to-noise and dynamic range of the received signals. FIG. 9B illustrates the method of combining processed pixel signals from multiple transmit-receive acquisitions to enhance some aspect of the pixel signal. In the text above, this method was used for combining data from a varying number of transmit-receive acquisitions for each pixel, where the number is based on a computation of the media motion relative to the transducer at the pixel location.

Finally, in FIG. 9C illustrates the de-coupling of the processing of pixel data sets or image frames from the acquisition process. In this case, the acquisition signals required to produce an image are grouped into data sets, which consist of one or more acquisition signal arrays. The storage area is made large enough to store many of these data sets, which can be written to in a circular manner. In this method, the acquisition of echo signal data can be performed at a high rate limited only by speed of sound considerations, while the processing of pixel signals proceeds at a lower rate suitable for display. When the acquisition is stopped, all data sets can be processed at a lower rate to provide a slow motion display.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of processing ultrasound acoustic data of media insonified by an ultrasound transducer, the method comprising:

determining a level of relative motion between the insonified media and the ultrasound transducer at spatial points in the media;

acquiring the acoustic data of the insonified media from the ultrasound transducer and storing the acquired data in memory, the acquiring the acoustic data including:

generating an acoustic signal;

receiving at least one echo of the acoustic signal at a plurality of receiving elements on the ultrasound transducer and obtaining an echo signal therefrom; and storing each echo signal from each of the plurality of receiving elements to form the stored acquired data;

determining, from the level of relative motion between the insonified media and the ultrasound transducer at each of the spatial points, an amount of the stored acquired data to use in generating an image point of the insonified media for each corresponding spatial point in which the amount of the stored acquired data used in generating each individual image point is dependent on the determined level of relative motion for the corresponding spatial point; and processing the determined amount of the stored acquired data to generate each of the image points of the insonified media for display, the processing the determined amount of the stored acquired data includes:

mapping a given pixel into a region of the stored echo signals in the memory, which comprises determining sample points in the stored acquired data that correspond to a spatial location of the given pixel relative to a respective transducer element;

determining from the level of relative motion between the insonified media and the ultrasound transducer at the pixel's spatial location the amount of the stored acquisition data to use in generating the image of the insonified media at the pixel location; and organizing the determined sample points of the stored acquired data into an array for the given pixel;

processing the array to generate a response for the given pixel; and using the response to obtain acoustic information for the given pixel.

2. The method of claim 1, wherein processing the determined amount of the stored acquired data comprises using at least one subset of the acquired data when the level of the relative motion of the insonified media at the respective spatial point is greater than a relative motion limit and otherwise using all of the acquired data.

3. The method of claim 1, wherein processing the determined amount of the stored acquired data comprises using at least one subset of the stored acquired data when the level of the relative motion at the respective spatial point is greater than a relative motion limit and using at least one additional subset of the stored acquired data when the level of the relative motion falls below one or more descending motion limits.

4. The method of claim 1, wherein acquiring the acoustic data comprises transmitting a planar or near-planar wavefront acoustic signal.

5. The method of claim 4, wherein acquiring the acoustic data comprises obtaining multiple transmit and receive data acquisitions using a plurality of steering angles of a planar or near planar wavefront acoustic signal.

6. The method of claim 1, wherein acquiring the acoustic data comprises using frequency compounding over multiple transmit and receive data acquisitions.

7. The method of claim 1, wherein acquiring acoustic imaging data comprises using spatial compounding over multiple transmit and receive data acquisitions.

8. An ultrasound processing method for displaying images of target media, comprising:

generating an acoustic signal with a transducer;

receiving at least one echo from the acoustic signal and acquiring echo signal data therefrom, and detecting relative motion between the transducer and the media insonified by the acoustic signal from the transducer at one or more spatial points in the insonified media;

storing in a memory the acquired echo signal data from each of a plurality of receiving elements in the transducer;

mapping a given pixel into a region of the stored acquired echo signal data, which comprises determining sample points in the stored acquired echo signal data that correspond to a spatial point location in the insonified media that in turn corresponds to the given pixel;

organizing the mapped region of the stored acquired echo signal data into an array for the given pixel; and determining whether a level of the relative motion between the transducer elements and the spatial point location in the insonified media for the given pixel exceeds a limit of relative motion, and processing a matrix array for the given pixel using a subset of the stored acquired echo signal data for the given pixel when the relative motion exceeds the limit and otherwise using all of the stored acquired echo signal data when the relative motion does not exceed the limit in order to generate an image, and repeating the determining step for each given pixel to be used in generating the image.

9. The method of claim 8, wherein processing the matrix array for each given pixel using a subset of stored acquired echo signal data comprises using a first subset of the stored acquired echo signal data when the relative motion exceeds the limit and is below a first threshold, and using a second subset of the stored acquired echo signal data when the relative motion exceeds the first threshold.

10. The method of claim 8, wherein processing the matrix array for each given pixel comprises using a first subset of the stored acquired echo signal data when the relative motion exceeds the limit and is less than a first threshold, using a second subset of the stored acquired echo signal data when the relative motion is greater than the first threshold and less than a second threshold, and using a third subset of the stored acquired echo signal data when the relative motion is greater than the third threshold.

11. The method of claim 8, wherein detecting relative motion of the insonified media comprises determining the velocity of relative movement between the insonified media and respective transducer elements at one or more spatial points in the insonified media, and processing comprises utilizing the velocity to process the matrix array for each given pixel and generate at least a portion of an image therefrom.

12. The method of claim 11, wherein the velocity of the relative motion is used in processing to control a length of a reconstruction period for an image point.

13. The method of claim 12, wherein when the velocity of the relative motion is low, a longer reconstruction period is used and more of the stored acquired echo signal data is used.

14. The method of claim 13, wherein acquiring echo signal data comprises acquiring different spatial and frequency information.

15. An image reconstruction system for forming an image of media, the system comprising:

a data acquisition system adapted to insonify the media and then acquire data from the insonified media and to detect relative motion between spatial locations in the insonified media and a transducer using the acquired data, the data acquisition system including a memory structured to store the acquired data from the insonified media prior to beam forming, the data acquisition system further adapted to:

generate an acoustic signal;

receive at least one echo of the acoustic signal at a plurality of receiving elements on the ultrasound transducer and obtaining an echo signal therefrom; and store each echo signal from each of the plurality of receiving elements to form the stored acquired data;

a processor structured to determine relative media velocity at each of the spatial location from the detected relative motion, to set a reconstruction period for reconstructing an image point in the image associated with a spatial location of the insonified media based on the determined velocity, and determine an amount of stored acquired data to use during the reconstruction period for each image point in the image based on the setting of the reconstruction period in which the reconstruction period is variable as to each image point based on the relative motion between the insonified media and the transducer at each associated spatial location, the processor further structured to:

map a given pixel into a region of the stored acquired data in the memory by a determination of sample points in the stored acquired data that correspond to a spatial location of the given pixel relative to a respective transducer element;

determine from the level of relative motion between the insonified media and the ultrasound transducer at the pixel's spatial location the amount of the stored acquisition data to use to generate the image of the insonified media at the pixel location; and organize the determined sample points of the stored acquired data into an array for the given pixel;

process the array to generate a response for the given pixel; and use the response to obtain acoustic information for the given pixel; and a device coupled to the processor and structured to display an image of the insonified media using image points generated by the processor.

16. The system of claim 15, wherein the processor is adapted to use the determined amount of stored acquired data to reconstruct the image point for display.

17. The system of claim 15, wherein the data acquisition system comprises an ultrasound transducer structured to insonify the media to be imaged and to acquire the acoustic data from the insonified media for storage in the memory of the data acquisition system.

* * * * *